United States Patent [19]

Monteverde et al.

[11] Patent Number: 5,198,869
[45] Date of Patent: Mar. 30, 1993

[54] REFERENCE WAFER FOR HAZE CALIBRATION

[75] Inventors: Robert J. Monteverde, Cupertino; Bradley W. Scheer, Sunnyvale, both of Calif.

[73] Assignee: VLSI Standards, Inc., Mountain View, Calif.

[21] Appl. No.: 597,788

[22] Filed: Oct. 15, 1990

[51] Int. Cl.[5] .............................................. G01N 21/88
[52] U.S. Cl. .................................................. 356/243
[58] Field of Search ................. 356/30, 237, 243, 371, 356/445, 446; 250/252.1 A

[56] References Cited

U.S. PATENT DOCUMENTS

| | | | |
|---|---|---|---|
| 4,352,016 | 9/1982 | Duffy et al. | 250/358.1 |
| 4,352,017 | 9/1982 | Duffy et al. | 250/358.1 |
| 4,386,850 | 6/1983 | Leahy | 356/243 |
| 4,512,659 | 4/1985 | Galbraith et al. | 356/237 |
| 4,551,800 | 4/1985 | Harbeke et al. | 250/372 |
| 4,636,073 | 1/1987 | Williams | 356/243 |
| 4,766,317 | 8/1988 | Harbeke et al. | 250/358.1 |
| 4,770,536 | 9/1988 | Golberstein | 356/371 |
| 4,899,055 | 2/1990 | Adams | 250/372 |
| 4,925,298 | 5/1990 | Dobrilla | 356/30 |
| 5,004,340 | 4/1991 | Tullis et al. | 356/243 |

*Primary Examiner*—Richard A. Rosenberger
*Attorney, Agent, or Firm*—Schneck & McHugh

[57] ABSTRACT

A standard for calibrating a wafer surface inspection optical scanner, particularly a system for measuring haze. The referene wafer contains sections divided into subsections, each subsection having a quasi-random pattern of light scattering features on an otherwise polished surface of the wafer. The quasi-random pattern of features is formed by creating a random pattern of pits within tiny areas of the subsection and repeating that pattern. The random pattern of pits covers an area less than the area of the spot of a scanning beam used by the wafer surface inspection system. By randomizing the pattern of pits within the scanning beam, the scattered light does not produce interference patterns and thus the scattered light is more isotropic. A direct measurement of the amount of hazel on the reference wafer can be obtained from measuring the amount of scattered light caused by the pits. Since this level of scattering is known beforehand to correspond to a certain level of haze, the wafer surface inspection system can then be calibrated to accurately measure haze on surfaces of non-reference wafers.

19 Claims, 2 Drawing Sheets

REFERENCE WAFER FOR HAZE CALIBRATION

DESCRIPTION

1. Technical Field

The present invention relates to methods and apparatus for calibrating semiconductor wafer inspection optical scanners.

2. Background Art

Being able to accurately measure and detect haze on a semiconductor wafer has become important to wafer manufacturers because haze tends to act as background noise when trying to detect particles on a wafer surface using an optical wafer surface inspection system. This optical noise affects the sensitivity of the inspection system to the extent that haze may be detected as a particle or particles may be masked by the haze.

Haze is defined as a decrease in the smoothness of a wafer surface from the ideal due to imperfections in the surface, such as, minute steps, contaminants in the grain structure, and other surface defects which cause light scattering or absorption. Subjectively, a wafer surface with a high amount of haze appears dull while a wafer with little haze appears shiny.

Knowing the level of haze on a wafer surface would allow increased sensitivity in inspection systems for particle detection. This is important since the size of the particles which needs to be detected is increasingly very small, well below one micron.

A further concern with haze is that a wafer surface which has a high level of haze may compromise the workings of subsequent circuits patterned on the wafer. Thus it is important to detect these undesirable wafers prior to being patterned.

Various methods for measuring surface roughness of a semiconductor wafer have been proposed. In U.S. Pat. No. 4,511,800, to Harbeke et al, a method of determining the surface roughness and structure of silicon films is disclosed using reflectance. Harbeke et al. further discloses in U.S. Pat. No. 4,766,317, a method for determining the degree of amorphism, surface roughness, and presence of a contaminating film on the surface of a SIMOX article. In this method the reflectance of the SIMOX material is compared against a single crystalline silicon material using selected wavelengths.

In U.S. Pat. No. 4,770,536, Galberstein discloses a method for measuring the surface roughness of a wafer based on reflectivity.

Reflectivity has been used to measure other characteristics of a wafer surface. For example, in U.S. Pat. No. 4,925,298, Dobrilla discloses measuring the etch pit density by comparing the reflectivity of the subject wafer against a polished reference wafer. Likewise, in U.S. Pat. No. 4,899,055, assigned to assignee of the present invention, Adams discloses measuring film thickness using reflectance which is calculated from the measured amount of reflected light and comparing that with the amount of reflected light detected from a standard substrate of known reflectivity.

Though haze can be equated with surface roughness, the polished reference wafers only give a relative standard against which comparisons are made based on reflectivity. Thus, polished reference wafers do not provide a direct haze measurement which can be used to calibrate a surface scanner.

It is an object of the present invention to provide a haze standard test or reference wafer for direct calibration of optical surface inspection systems.

It is a further object of the present invention to provide a method for making a haze standard test or reference wafer.

SUMMARY OF THE INVENTION

The above objects have been achieved by producing a haze standard reference wafer for calibrating optical surface inspection systems in which a quasi-random pattern of light-scattering features are placed on a section of a surface of the wafer. Preferably the light-scattering features are in the form of pits because pits are generally easier to make than a raised bump, but the feature could be of either form. Though the haze standard is described as being a wafer, it can be a substrate of just about any form or shape, such as a reflective glass plate. A wafer is preferred because many inspection systems are designed to handle wafers. The present invention has particular use in wafer surface inspection systems which use optical scanning to detect particles and defects on a surface. One such surface scanner is described in U.S. Pat. No. 4,378,159, but other scanners may also be employed.

The quasi-random pattern of light scattering pits is formed on a silicon dioxide coated semiconductor wafer by dividing a section of the surface into several subsections. A subsection is then further divided into a matrix of tiny rectangular areas with dimensions of just a few microns per side. A random vector is then generated from a reference location within each tiny rectangle of the selected subsection. The random vectors are each defined by a x-y coordinate pair. A pit is then formed in each tiny rectangle at the coordinates of the corresponding x,y location. Pits are formed by etching into the silicon dioxide film which has been thermally grown on a polished silicon wafer. This creates a random pattern of pits within the selected subsection. This random pattern of pits is then repeated in the other subsections, thereby forming the quasi-random pattern of pits for the entire section.

In a preferred embodiment of the invention, the tiny rectangles have an area of 5×5 micrometers square and the subsections are 50×50 micrometers square. Each subsection is a 10×10 matrix of tiny rectangles, which in turn means that there are 100 x-y coordinate pairs for the tiny rectangles within a subsection. Subsections may be organized into larger patterns, termed sections. The light-scattering subsections or sections are distributed regularly over the surface of a wafer in desired positions where a scanning beam will encounter them.

The pattern of pits is random on a small scale (distances less than 50 micrometers) so that when a laser spot strikes the wafer surface, the light scattered from one pit interferes randomly with the light scattered from neighboring pits. By randomizing the pattern of pits within the laser spot, the scattered light does not produce an interference pattern and thus the scattered light is more isotropic.

The pattern of pits is regular on a large scale (distances greater than about 50 micrometers) so that wherever a laser spot strikes the wafer surface, it illuminates about the same number of pits. Therefore, the wafer surface scatters the same amount of light from any part of the patterned surface.

Advantages of the present invention are that a direct measurement of the amount of haze can be made using a standard reference wafer of known haze for the purpose of calibrating the wafer surface scanner. Further, the pattern of pits is random on a small scale so that when a laser spot strikes the wafer surface, the light scattered from one pit interferes randomly with the light scattered from neighboring pits. By randomizing the pattern of pits within the laser spot, the scattered light does not produce an interference pattern and thus the scattered light is more isotropic. Another advantage is that the pattern of pits is regular on a large scale so that wherever a laser spot strikes the wafer surface, it illuminates about the same number of pits. Therefore, the wafer surface scatters the same amount of light from any part of the patterned surface.

BEST MODE FOR CARRYING OUT THE INVENTION

Figure 1:
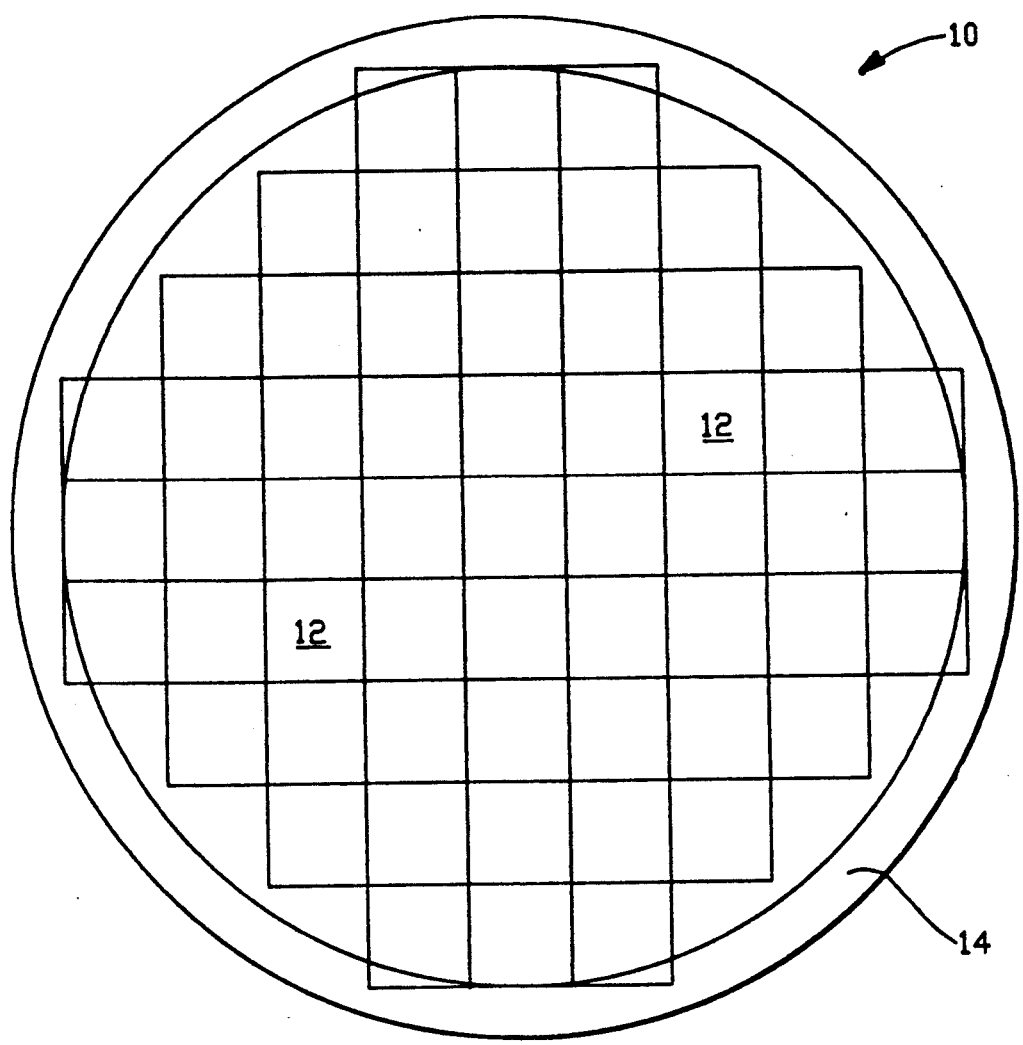
FIG. 1 is a top plan view of a wafer surface having been divided or sectored into a plurality of sections in accord with the present invention.

Referring to FIG. 1, a wafer 10 is shown divided into a plurality of imaginary sections 12. The wafer 10 is a highly polished semiconductor substrate as is known in the art, i.e. a bare wafer, with a thin coating of thermally grown silicon dioxide. The sections 12 are not physically marked on the wafer and do not extend all the way to the edge of the wafer, but a narrow band 14 is left around the outer edge of the wafer 10. The layout of the sections may be physically placed on a glass reticle and projected onto a wafer. The wafer 10 may be of size commonly used in the semiconductor industry.

Figure 2:
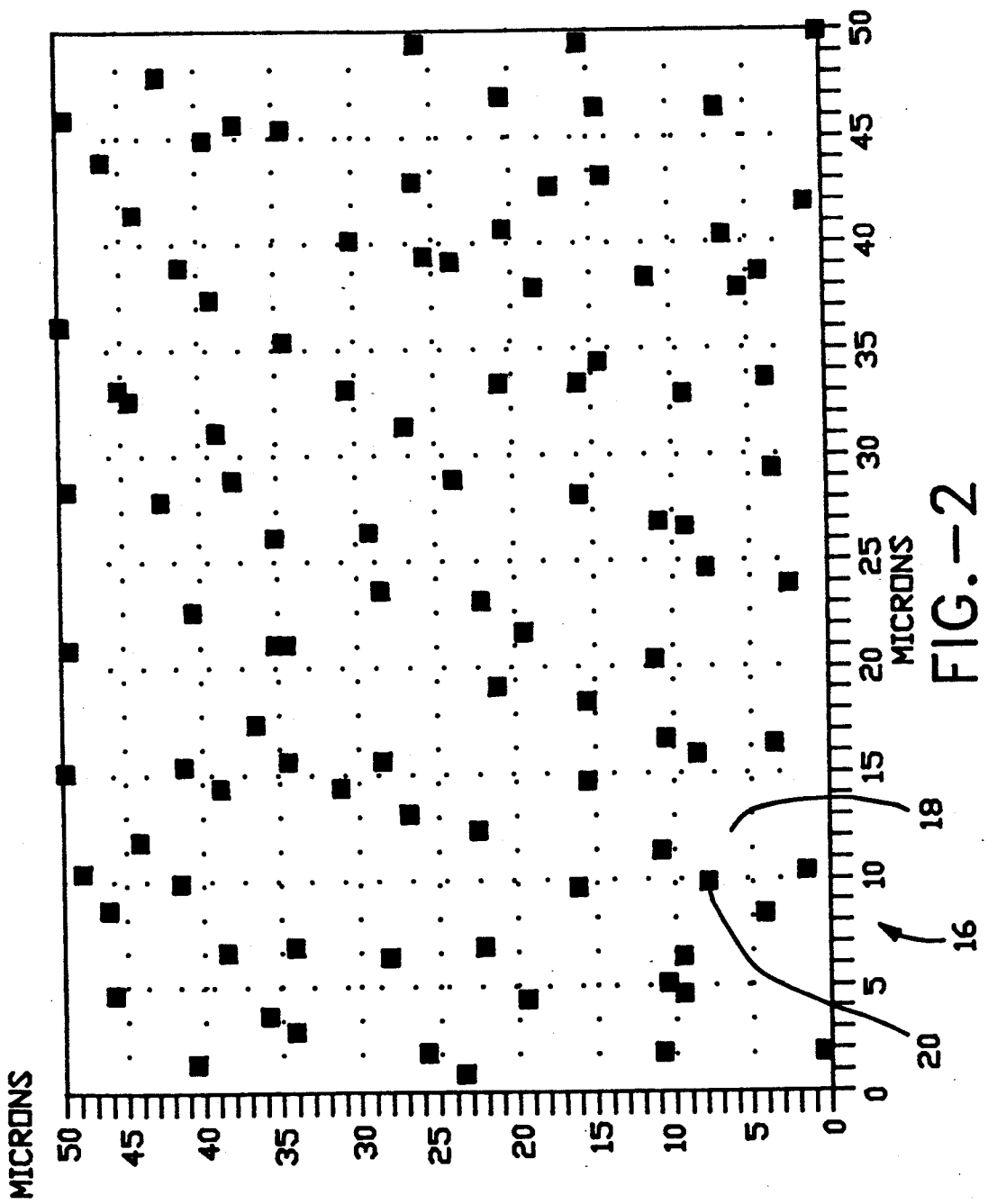
FIG. 2 is an enlarged view of one of the sections shown in FIG. 1.

Turning now to FIG. 2, each of the sections is subdivided into a grid pattern of subsections 16. The area of the individual subsection 16 should be less than the beam spot areas of the scanning laser which is expected to be used to inspect wafer surfaces. Each subsection 16 also contains a grid pattern of tiny rectangles 18, indicated by dotted lines, with each rectangle containing a randomly located pit. The randomly located pit 20 needs to be substantially smaller in area than the scanning beam. Since the typical scanning beam diameter is about 100 μm, an area of 50 μm by 50 μm for the subsections is a good choice, providing a good number of pits which are illuminated by the beam.

Figure 3:
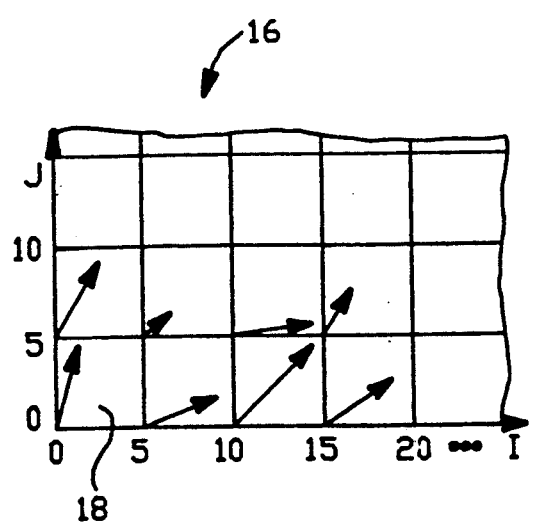
FIG. 3 is an enlarged view of a portion of the section shown in FIG. 2.

Turning now to FIG. 3, a portion of one of the subsections 16 is shown having been subdivided into a matrix of tiny rectangular areas indicated by solid lines. In a preferred embodiment, a subsection 16 contains a 10×10 matrix or grid of such tiny rectangles. Following the dimensions of the preferred embodiment, each rectangle 18 is 5 μm by 5 μm square but could range in area from 10 square μm to 100 square μm. It is within one of these subsections 16 that the random pattern of pits is created and then repeated in the other subsections.

One pit is randomly located within each of the tiny rectangles 18. The location of these pits is determined from the coordinates of a random vector. These coordinates, x and y, are measured from the lower leftmost corner point for a given tiny rectangle. For the general situation where the tiny rectangles 18 have an area of "A" by "A" square and the subsections are a "B" by "B" matrix of squares, then the coordinate pairs are given by the following equations:

$$x_n = i + \text{"A"} * Rand$$

$$y_n = j + \text{"A"} * Rand$$

where
  $n = 0, 1, 2, \ldots B^2 - 1$
  $i = 0, A, 2A, \ldots, (B-1)A$
  $j = 0, A, 2A, \ldots, (B-1)A$
  Rand = any randomly generated number from 0.0 to 1.0 inclusive;
  thereby forming a random pattern of pits.

This random subsection pattern is then repeated in the other subsections thereby forming the quasi-random pattern of pits for the entire section. Sections are repeated or may be different as to random feature patterns, but the same as to feature density per unit area. In a preferred embodiment "A" = 5 μm, "B" = 10 μm and the section contains (20×20) subsections. Thus, in this embodiment the random pattern is repeated twenty times in both the i and j directions for a total section size of 1000 μm × 1000 μm (1 mm × 1 mm). This results in having 40,000 pits in the section 12. Other sections 12 are formed in the same manner.

It is noted that the periodicity of the random pit pattern is related to the laser beam diameter. Therefore, the size of the subsections and tiny rectangles should be designed accordingly, dependent upon the expected diameter of the scanning beam.

The light scattering pits used in this invention can be formed using several different methods, but etching of the silicon dioxide film on the surface is preferred because it is a process that is well known within the semiconductor industry. Further, etching makes use of photomasks which provide better repeatability than say direct laser ablation methods. Accordingly, a mask is formed, either positively or negatively depending on the etchants used, with a quasi-random pattern of openings or opaque areas which match the desired quasi-random pattern of pits. The etching process is then carried out as is well known in the art resulting in a haze standard reference wafer.

Scattering from a reference wafer is measured and correlated to scattering from wafers with haze corresponding to a known amount of surface roughness. In this matter the reference wafer can be used to calibrate the surface scanner.

Once this has been done, haze on an unknown wafer may be readily measured. Similarly, scattering from other reference wafers with different densities or sizes of light scattering features may be correlated with scattering from wafers with known amounts of surface roughness. Then, a surface with unknown roughness is scanned and the amount of light scattering from the surface is compared with the previously scanned reference surfaces and one of the reference surfaces is identified as the one having the closest amounts of scattered light in relation to the unknown surface.

We claim:

1. A reference for haze calibration of a wafer scanner comprising,
  a wafer having a plurality of light scattering features fabricated on a substrate thereof within an imaginary regular array of cells such that the position of each of said scattering features coincides with a calculated random location within a cell, each cell having one and only one scattering feature therein, said cells having a maximum size of 100 square micrometers.

2. The wafer of claim 1 wherein said regular array is a hierarchical system comprising sections forming an ordered collection of subregions, each subregion being an ordered collection of similar cells.

3. The wafer of claim 2 wherein said subregions are identical.

4. The wafer of claim 1 wherein said cells are rectangular.

5. The wafer of claim 4 wherein said rectangular cells are square.

6. The wafer of claim 2 wherein all of said cells within at least each subregion have the same size, said size being in a range from 10 square micrometers to 100 square micrometers.

7. The wafer of claim 1 wherein said light scattering features are disposed in a planar surface.

8. The wafer of claim 1 wherein said regular array of cells has dimensions such that a scanning beam having a diameter of 100 μm illuminates from fifty to four hundred scattering features.

9. The wafer of claim 1 wherein said substrate has a thin film coating, said light scattering features comprising surface relief in said thin film.

10. The wafer of claim 1 wherein said light scattering features extend over the surface of the substrate except for an annular band about the periphery of the substrate.

11. A reference surface for calibration of wafer surface haze measurement equipment comprising,
a substrate having a surface and a plurality of light scattering features fabricated thereon, said features having positions on said surface coinciding with calculated random locations within a regular pattern of surface regions, said pattern having a plurality of scales, said scales ranging from a smallest scale corresponding to tiny areas of said surface on the order of said features to a largest scale on the order of one-fourth of a wafer, each tiny area of said surface at said smallest scale of said regular pattern having one and only one light scattering feature positioned therein, such that on scales larger than said smallest scale there exists a uniform areawise density of light scattering features on said surface, said tiny areas of said surface having dimensions substantially less than a spatial resolution of a 100 μm scanning beam.

12. The apparatus of claim 11 wherein said rectangular tiny areas are square.

13. The apparatus of claim 11 wherein said smallest scale has a size within a range from 1 micrometer to 10 micrometers.

14. The apparatus of claim 11 wherein said light scattering features are disposed in a planar surface.

15. The apparatus of claim 11 wherein said substrate is on a wafer of the type used in manufacturing semiconductor integrated circuits.

16. The apparatus of claim 15 wherein said wafer has a thin film coating forming said reference surface, said light scattering features comprising surface relief in said thin film.

17. A method for forming a base reference standard for calibrating an optical surface scanner having a scanning beam with a beam spot comprising,
dividing a planar surface into a plurality of subregions,
dividing each subregion into tiny areas where there are at least 50 tiny areas per subregion, and
generating a randomly placed light scattering feature in each tiny area.

18. The method of claim 17 wherein the subregions are identical.

19. The method of claim 17 further defined by forming a grid pattern of subregions on said reference surface pattern.

* * * * *